US00PP14970P3

(12) United States Plant Patent
Yamamoto

(10) Patent No.: US PP14,970 P2
(45) Date of Patent: Jun. 29, 2004

(54) HYDRANGEA SERRATA PLANT NAMED 'OKAN'

(50) Latin Name: *Hydrangea serrata*
Varietal Denomination: Okan

(75) Inventor: Takeomi Yamamoto, Tokyo (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 10/212,948

(22) Filed: Aug. 5, 2002

(65) Prior Publication Data

US 2004/0025213 P1 Feb. 5, 2004

(51) Int. Cl.[7] ..... A01H 5/00
(52) U.S. Cl. ..... Plt./250
(58) Field of Search ..... Plt./250

(56) References Cited

U.S. PATENT DOCUMENTS

| | | | | | |
|---|---|---|---|---|---|
| PP276 | P | * | 4/1938 | Kluis | Plt./250 |
| PP2,265 | P | * | 6/1963 | Cayeux | Plt./250 |
| PP2,266 | P | * | 6/1963 | Cayeux | Plt./250 |
| PP6,924 | P | * | 7/1989 | Sakamoto | Plt./250 |
| PP10,912 | P | * | 5/1999 | Rampp et al. | Plt./250 |
| PP10,928 | P | * | 6/1999 | Rampp et al. | Plt./250 |
| PP10,930 | P | * | 6/1999 | Rampp et al. | Plt./250 |

* cited by examiner

*Primary Examiner*—Bruce R. Campell
*Assistant Examiner*—W C Haas
(74) *Attorney, Agent, or Firm*—Christie, Parker & Hale, LLP

(57) ABSTRACT

A new plant variety of *Hydrangea serrata* characterized by its golden yellow to chartreuse foliage coloration which persists throughout the growing season.

3 Drawing Sheets

Botanical name: *Hydrangea serrata* (Thunb. ex J. A. Murr.) Ser. 'Okan'.

BACKGROUND OF THE INVENTION

The present invention relates to a new and distinct variety of *Hydrangea serrata* (Thunb. ex J. A. Murr.) Ser. which was discovered by Mr. Takeomi Yamamoto as a seedling selection in a controlled planting of *Hydrangea serrata* in Nerima-Ku, Tokyo, Japan. The varietal denomination of the new variety is 'Okan'.

The genus Hydrangea is included in the family Saxifragaceae which comprises about 80 genera and 1,200 species of herbs, shrubs, small trees and woody climbers mostly temperate in origin. Hydrangea comprises approximately 23 species of deciduous or evergreen shrubs and vines originating in North America, South America and East Asia, many of which possess desirable ornamental characteristics. Recent taxonomical treatments sometimes isolate Hydrangea in a new family, Hydrangeaceae.

*Hydrangea serrata* is widespread and common throughout much of Japan, Korea and China. It generally has opposite, simple leaves, lanceolate in shape with acuminate apices, 5 to 15 cm long and 5 to 10 cm wide. Leaf color ranges from light to dark green, depending on light intensity and cultural conditions. Leaves are generally softly pubescent. The plant is deciduous. Flower color is dependent upon the pH level of the soil and the amount of available aluminum in the soil media. Flowers of *Hydrangea serrata* are borne in mostly flattened corymbs, 1 to 5 cm wide, with up to 12 sterile florets.

SUMMARY OF THE INVENTION

The new variety was discovered as a seedling selection in a controlled planting of *Hydrangea serrata* (unnamed, undistributed and unpatented) and differs from its parent in having golden yellow to chartreuse foliage throughout the growing season. Asexual reproduction of the new variety by stem cuttings performed in Tokyo, Japan; Lewisberry, Pa.; and Vacaville, Calif. have confirmed that the distinctive characteristics of the new variety are stable and transmitted to succeeding generations, and the new variety reproduces true to type.

COMPARISON WITH PARENT

'Okan' is distinguished from its parent and all other varieties of *Hydrangea serrata* of which I am aware by its golden yellow to chartreuse foliage coloration which persists throughout the growing season.

BRIEF DESCRIPTION OF ILLUSTRATIONS

The accompanying photographic illustrations show a specimen of the new cultivar as true to color as is reasonably possible to make in an illustration of this character.

DESCRIPTION OF THE NEW VARIETY

Figure 1:
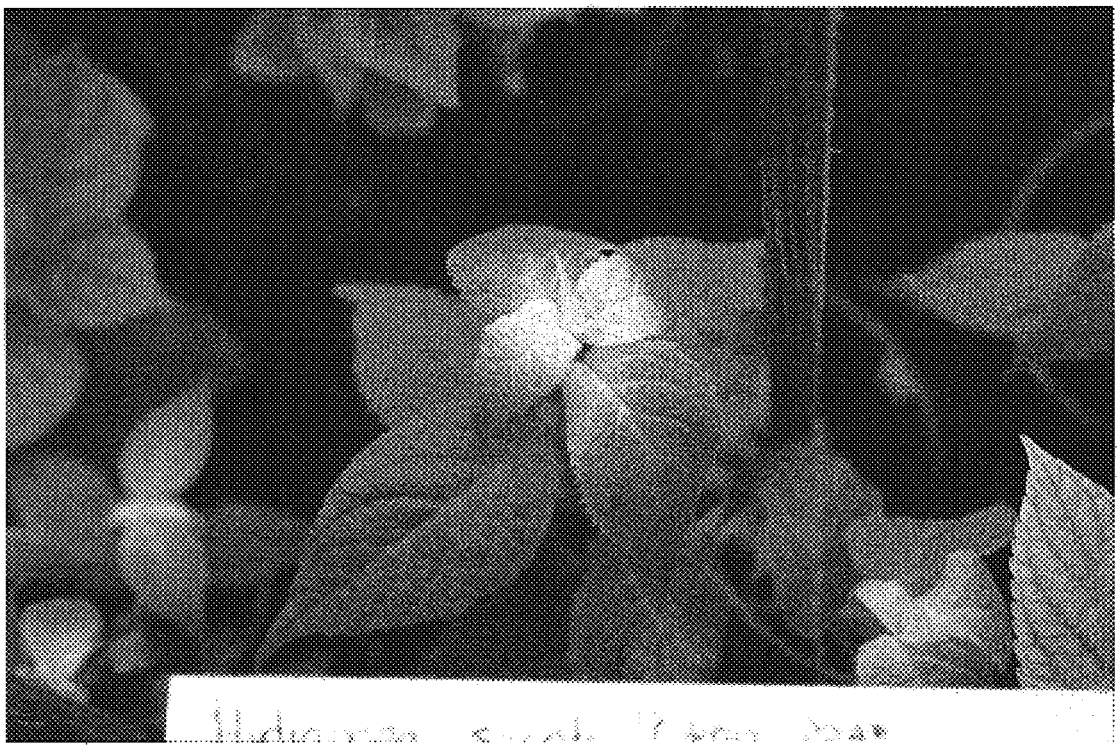
FIG. 1 illustrates the characteristic golden-yellow foliage of 'Okan' (grown under 50% shade).
Figure 2:
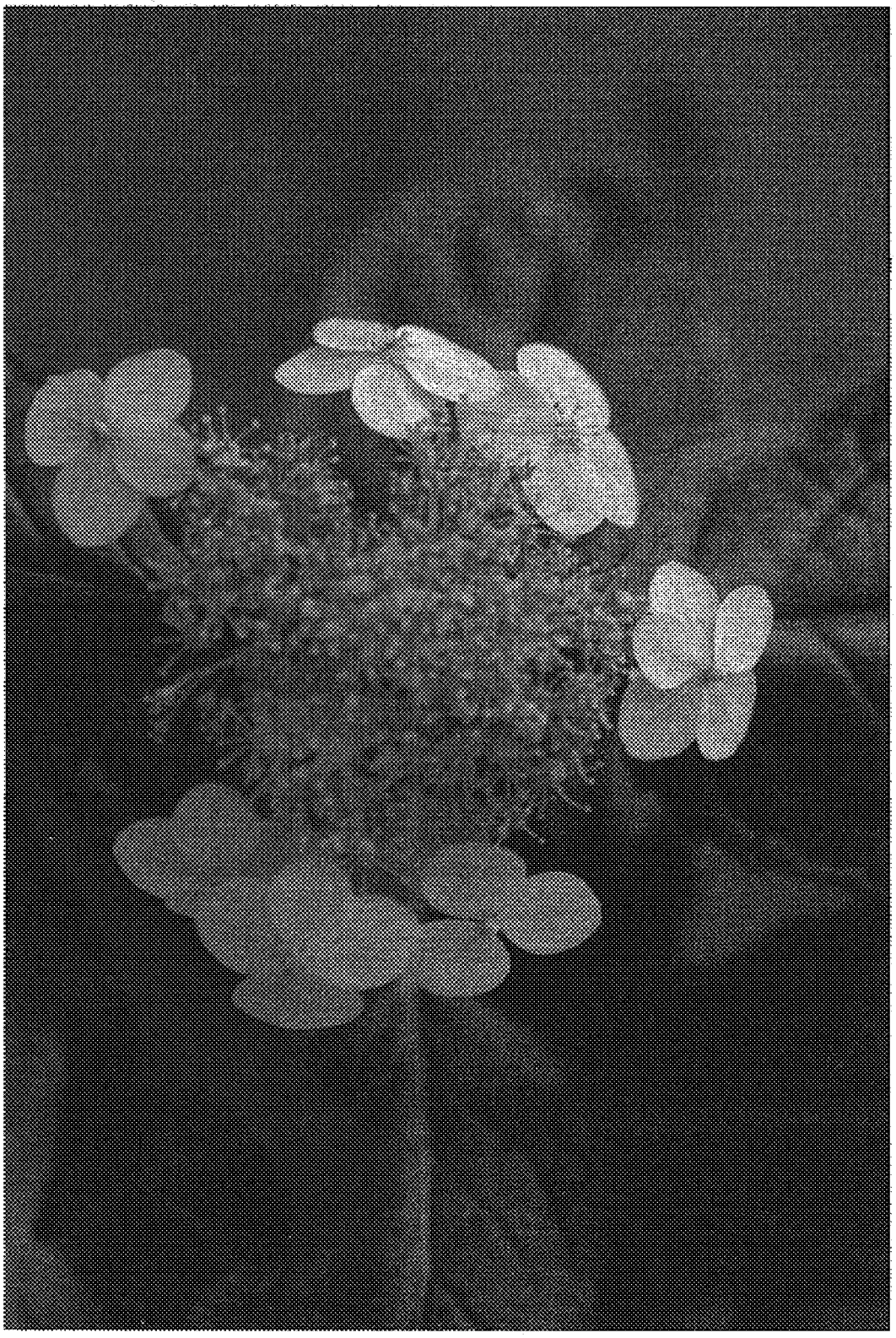
FIG. 2 illustrates the typical flower form (soil and water pH levels of 6.4).
Figure 3:
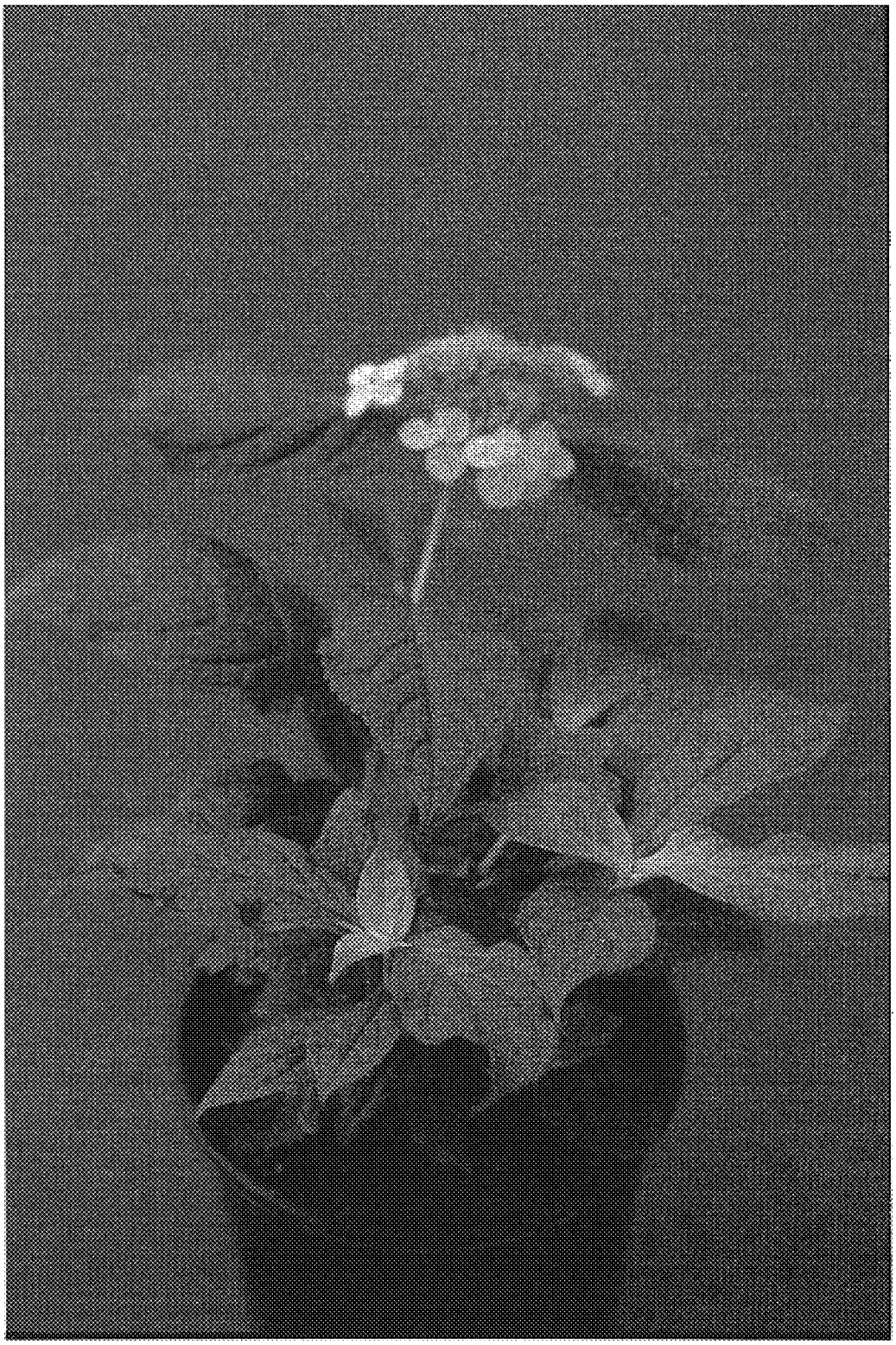
FIG. 3 illustrates the overall growth habit, the flower position on the plant and the characteristic golden-yellow foliage of 'Okan'.

'Okan' has not been observed under all possible environmental, cultural and light conditions. The following observations and descriptions are of plants grown in containers in Lewisberry, Pa., and Vacaville, Calif. In this description, color references are to The Royal Horticultural Society Colour Chart (2001) and terminology used in the color descriptions herein refers to plate numbers in this color chart. Phenotype expression may vary with light intensity, cultural, and environmental conditions.

Classification:

*Botanical.*—*Hydrangea serrata* (Thunb. ex J. A. Murr.) Ser. 'Okan'.

*Parentage.*—Seedling selection of *Hydrangea serrata.*

*Propagation.*—By vegetative cuttings.

PLANT

*Age of observed plant.*—2-year-old plant in a 1-gallon nursery container.

*Typical age of maturity.*—4 to 5 years.

*Size.*—To 1 m high and 1 m wide at maturity.

*Habit.*—Mounding deciduous shrub with upright, or obliquely spreading branches.

*Branching.*—Freely branching on 1 year-old wood. Lateral branches: 8. Typical number of branches: 35. Observed number of branches: 8. Size: About 40 cm long.

*Diameter.*—About 5 mm.

*Color.*—Near Yellow-Green Group 144D.

*Color of new shoots.*—Near Yellow-Green 144D.

*Internode length on branches.*—2 to 4 cm.

*Branch texture.*—Smooth.

*Lenticels.*—Not visible with hand lens.

Leaf:

*Shape.*—Ovate to long-ovate occasionally oblong.

*Leaf base.*—Mostly cuneate, occasionally attenuate.

*Leaf apex.*—Acuminate.

*Leaf size.*—Up to 12 cm long and 5.5 cm wide.

*Arrangement.*—Opposite.

*Margin.*—Coarsely serrate.

*Texture/substance.*—Dull to nearly glabrous with scattered fine white hairs above, nearly glabrous and glossier with very few tiny hairs beneath; texture chartaceous to firm.

*Color.*—The following color readings are of mature specimens of 'Okan' grown in nursery conditions under 50% shade. Leaf color is generally yellow early in the growing season tending toward chartreuse as the foliage ages. Color varies with intensity of sunlight and cultural conditions. Young foliage Upper side: Near Green-Yellow Group 1B. Underside: Near Green-Yellow Group 157B. Mature foliage Upper surface: Ranging from near Yellow Group 7B to 13C (unshaded leaves); near Green Group 143A to 143C (leaves shaded by flowers, other leaves) Under surface: Near Green Group 143B to 143D. Venation Pattern Upper surface: Alternately pinnate, depressed. Under surface: Raised. Petioles Size: From 3.5 to 5 mm long and 1 mm in diameter. Color: Near Yellow-Green Group 144D. Texture: Finely dentate.

*Hardiness.*—USDA Zone 5 (−20° to −10° F.).

*Vigor.*—Fast growth rate typical for Hydrangeas.

*Pests/diseases.*—No susceptibility or resistance to disease beyond that of the species has been noted.

Inflorescence:

*Bloom period.*—Outdoors: Spring to Summer. Greenhouse: Not evaluated in a greenhouse setting. Flower form: Corybose, with 400 or more individual florets per inflorescence. 10 or more sterile florets and 100 or more fertile florets. Both sterile, sepalous florets and fertile, non-sepalous florets borne within the same corymb. Flower arrangement: In a flattened corymb Flower size: Approximately 15 cm in diameter.

*Shape of inflorescence.*—Flattened corymose cluster of numerous small florets.

*Fragrance.*—None noted.

*Lastingness of individual blooms.*—Flowers persist, lasting up to 4 to 5 months.

*Sepals.*—Number: 4 to 5 per floret; usually 4. Shape: Ovate Size: To 2.2 mm long and 3.0 mm wide; each sterile floret usually includes 1 dominant sepal, 2 equal and smaller sepals, and 1 yet smaller sepal. Sepals elongate and become pigmented as the inflorescence matures. Margin: Serrate. Arrangement: Overlapping. Size of one 4-sepaled floret: To 2 cm in diameter. Color: Near Blue Group 106C (soil pH level of 6.4).

*Non-sepalous florets.*—Size of floret: 2 to 3 mm. Color of floret: Near Blue Group 106B (soil pH level of 6.4).

Reproductive organs:

*Androecium.*—Stamens: 7 to 9. Anthers: Size about 1 to 2 mm. Filament Color: Near Blue Group 106C. Pollen amount: Tiny, not measurable. Pollen color: Near White Group 155D.

*Gynoecium.*—Pistil length: 1 to 2 mm. Stigma: 13-pronged stigma. Stigma color: Near blue Group 106C.

*Fruit.*—None noted.

I claim:

1. A new and distinct variety of Hydrangea plant, as illustrated and described.

* * * * *